United States Patent
Stikvoort (10) Patent No.: US 11,564,339 B2
(45) Date of Patent: Jan. 24, 2023

(54) ELECTRICAL DEVICE COMPRISING FILTER AND FEEDTHROUGH CAPACITOR

(71) Applicant: ENRAF-NONIUS B.V., Rotterdam (NL)

(72) Inventor: Raymundus Johannes Stikvoort, Rotterdam (NL)

(73) Assignee: ENRAF-NONIUS B.V.

( * ) Notice: Subject to any disclaimer, the term of this patent is extended or adjusted under 35 U.S.C. 154(b) by 408 days.

(21) Appl. No.: 16/603,758

(22) PCT Filed: Apr. 11, 2018

(86) PCT No.: PCT/EP2018/059256
§ 371 (c)(1),
(2) Date: Oct. 8, 2019

(87) PCT Pub. No.: WO2018/189226
PCT Pub. Date: Oct. 18, 2018

(65) Prior Publication Data
US 2020/0137932 A1    Apr. 30, 2020

(30) Foreign Application Priority Data
Apr. 11, 2017  (EP) .................................. 17166094

(51) Int. Cl.
*A61N 1/32* (2006.01)
*H01G 4/35* (2006.01)
(Continued)

(52) U.S. Cl.
CPC ............. *H05K 9/0033* (2013.01); *A61N 1/32* (2013.01); *H01G 4/35* (2013.01); *H01G 4/38* (2013.01);
(Continued)

(58) Field of Classification Search
CPC .... H05K 9/0033; H05K 1/0231; H05K 1/115; H05K 9/0039; H05K 2201/09227;
(Continued)

(56) References Cited

U.S. PATENT DOCUMENTS 5,285,007 A * 2/1994 Deluca ................ H05K 9/0037
174/360
5,590,029 A * 12/1996 Estes ...................... H05K 1/184
361/783
(Continued)

FOREIGN PATENT DOCUMENTS

| CN | 201490970 U | 5/2010 |
|---|---|---|
| JP | 06268464 A | 9/1994 |
| JP | 2004207419 A | 7/2004 |

OTHER PUBLICATIONS

International Search Report and Written Opinion for International Application No. PCT/EP2018/059256 (12 pages).

*Primary Examiner* — Timothy J Thompson
*Assistant Examiner* — Michael F McAllister
(74) *Attorney, Agent, or Firm* — Mendelsohn Dunleavy, P.C.

(57) ABSTRACT

An electrical device (1) is provided, comprising an electrical high-frequency filter (9) and a shield (6) separating the filter from at least one further electrical component (9, 13) of the device, a signal conductor (17) which operably connects the filter (9) to the further component (9, 13) and traverses the shield (6) for transmitting a signal from the filter (9) to the component (9, 13) and a feedthrough capacitor system (19) being electrically arranged between the signal conductor (17) and the shield (6). The feedthrough capacitor system (19) comprises, in particular being formed essentially by, a plurality of surface mount capacitors (41) electrically arranged between the signal conductor (17) and the shield (6), the surface mount capacitors (41) in particular being
(Continued)

surface mounted on a circuit board (11), which may be a printed circuit board.

22 Claims, 4 Drawing Sheets

(51) Int. Cl.
    *H01G 4/38*       (2006.01)
    *H05K 9/00*       (2006.01)
    *H05K 1/02*       (2006.01)
    *H05K 1/11*       (2006.01)

(52) U.S. Cl.
CPC ........... *H05K 1/0231* (2013.01); *H05K 1/115* (2013.01); *H05K 9/0039* (2013.01); *H05K 2201/093* (2013.01); *H05K 2201/09227* (2013.01); *H05K 2201/10015* (2013.01); *H05K 2201/10522* (2013.01)

(58) Field of Classification Search
CPC ... H05K 2201/093; H05K 2201/10015; A61N 1/32; H01G 4/35; H01G 4/38
USPC .......................................................... 607/115
See application file for complete search history.

(56) References Cited

U.S. PATENT DOCUMENTS

| | | | |
|---|---|---|---|
| 5,830,016 A * | 11/1998 | Chuang | H01R 13/6666 439/620.09 |
| 5,895,980 A * | 4/1999 | Thompson | A61N 1/37512 607/36 |
| 5,896,267 A * | 4/1999 | Hittman | H03H 1/0007 29/25.42 |
| 5,959,829 A * | 9/1999 | Stevenson | H03H 1/0007 333/182 |
| 5,973,906 A * | 10/1999 | Stevenson | H01G 4/35 361/306.1 |
| 6,377,845 B1 * | 4/2002 | Kinast | A61B 5/30 600/547 |
| 6,424,234 B1 * | 7/2002 | Stevenson | A61N 1/3752 333/182 |
| 6,473,314 B1 | 10/2002 | Custer et al. | |
| 6,778,040 B2 * | 8/2004 | Kim | H05K 9/0066 333/182 |
| 7,295,086 B2 * | 11/2007 | Van Hoyweghen, III | H01G 4/35 333/182 |
| 9,248,283 B2 * | 2/2016 | Halperin | G01R 33/287 |
| 2004/0012462 A1 * | 1/2004 | Kim | H01R 13/719 333/182 |
| 2004/0212971 A1 * | 10/2004 | Iguchi | H01L 24/16 361/780 |
| 2005/0022744 A1 | 2/2005 | Natsuhara et al. | |
| 2007/0071886 A1 | 3/2007 | Babb et al. | |
| 2007/0123949 A1 * | 5/2007 | Dabney | H03H 1/0007 607/37 |
| 2008/0195180 A1 * | 8/2008 | Stevenson | A61N 1/05 607/60 |
| 2015/0173174 A1 * | 6/2015 | Wei | H05K 1/0231 361/782 |
| 2016/0151635 A1 * | 6/2016 | Frysz | A61N 1/3754 607/119 |
| 2018/0077791 A1 * | 3/2018 | Barry | H05K 3/4038 |
| 2018/0207428 A1 * | 7/2018 | Barry | H05K 5/0247 |

\* cited by examiner

ELECTRICAL DEVICE COMPRISING FILTER AND FEEDTHROUGH CAPACITOR

TECHNICAL FIELD

The present disclosure relates to electrical devices comprising high frequency filtering circuits, in particular for high powers. More in particular, the present disclosure relates to an electrical device comprising an electrical high-frequency filter and a shield separating the filter from at least one further electrical component of the device, a signal conductor which operably connects the filter to the further component and traverses the shield for transmitting a signal from the filter to the component, and a feedthrough capacitor system being electrically arranged between the signal conductor and the shield.

BACKGROUND

Electrical devices according to the above are used for filtering oscillatory electrical signals commonly referred to as AC signals. High-frequency AC power generators and/or amplifiers may generate electromagnetic noise to other components in a device comprising the generator and/or in other devices. To prevent such noise, filtering of the noise from the desired AC signal and shielding are desired. Also, sensitive AC equipment may require shielding and filtering, e.g. against outside noise.

The signal conductor for carrying the signal that is (to be) filtered is arranged for transmitting the signal from the filter to the component. The feedthrough capacitor system is operably electrically arranged between the signal conductor and the shield wall, e.g. to reduce losses at the traverse of a signal transmitted from the filter to the component along the signal conductor and/or to reduce noise transmission along and/or through the traverse.

Different systems employing a feedthrough capacitor are known, see e.g. 4 US2005/0022744, JP 2004-207419, CN 2014490970U.

Commercially available feedthrough capacitors are available in a variety of combinations of properties such as capacitance, rated current and rated voltages. However, production and sale of feedthrough capacitors suitable for medium to high power radio-frequencies has been largely discontinued, leading to price increases and putting future replacement and/or repair of devices provided with such capacitors at risk. Moreover, presently available standard capacitors with wire terminals exhibit large series-inductances which limits performance achievable for filtering.

Surface mount ceramic feedthrough capacitors (also referred to as Surface Mount Device ceramic feedthrough capacitors or SMD ceramic feedthrough capacitors) are known and they enable a small mounting volume and a small series-inductance. However, such feedthrough capacitors tend to be expensive and to be commercially available only in limited combinations of properties like capacitance, rated current and rated voltages.

Further improvements are therefore desired, e.g. regarding at least one of filtering, noise reduction, allowable operational power, and manufacturing cost of the electrical device.

SUMMARY

In view of the above considerations, in an aspect a device of the aforementioned type is provided wherein the feedthrough capacitor system comprises, in particular being formed essentially by, a plurality of surface mount capacitors electrically arranged between the signal conductor and the shield.

The electrical device may be a power source, an amplifier, a transmitter, and/or a receiver a detector, etc.

Surface mount capacitors are generally ceramic or other dielectric-based low form factor capacitors that can be soldered directly onto a carrier such as a (printed) circuit board, without contact leads like wires or screw-mounts protruding from the capacitors. Constructing a feedthrough capacitance structure with a plurality of surface mount capacitors enables providing a wide variety of capacitances with comparably low series inductance and with current and voltage capacities suitable for transmitting high power radio-frequency signals at low or no loss of signal power and/or signal quality. Also, suitable shielding can be provided for the shield traverse of the signal conductor.

The circuit board may electrically insulate the signal conductor from the shield.

The plurality of surface mount capacitors may be surface mounted on a circuit board, which may be a printed circuit board. This facilitates manufacturing and enables reducing volume of the device. Positioning of the capacitors may also be accurately determined which may improve filtering behaviour, in particular predictability thereof.

In an embodiment, the filter is a filter segment and the further electrical component is a further filter segment, the filter segments together forming at least part of a sequential filtering device. This improves filtering in the device and it allows reducing construction volume of the device.

In an embodiment, the shield is part of a housing at least partly surrounding the filter. In case of a sequential filtering device, the housing may at least partly surround and shield the whole sequential filtering device or only one or more filter segments thereof and plural such housings each at least partly surrounding and shielding at least one of the filter segments may be provided. A shield may be shared between adjacent housings, e.g. forming a wall shared by two adjoining housings and/or dividing a larger two housing into two partial housings e.g. as compartments of a larger housing. Conductive housings surrounding the filter (segment) provide shielding in all associated directions. A ground plane of the circuit board may provide one conductive wall of such housing.

In an embodiment, in the feedthrough capacitor system the signal conductor extends at least partly on and/or in the circuit board as a signal trace on and/or in the circuit board and/or as a signal via through at least part of the circuit board.

In an embodiment the circuit board comprises a ground trace and/or a conductive ground via which is electrically connected to the shield, preferably also being mechanically attached to the shield. This reduces potential differences between the conductive shield and the ground trace. A mechanical connection increases structural stability and may prevent noise leaking.

In a further developed embodiment, the surface mount capacitors are surface mounted to the signal trace and to the ground trace. This facilitates manufacturing and reliability of the device.

In an embodiment, a plurality of the one or more surface mount capacitors is mounted symmetrical around at least part of the signal portion on the circuit board, in particular substantially radially symmetric around at least part of the signal portion on the circuit board, more in particular substantially radially symmetric around a via. A symmetric arrangement, in particular with all capacitors being arranged at a substantially constant distance, or at least a substantially equal signal travelling time, from the signal conductor tends to improve signal quality relative to an asymmetric arrangement. A radially symmetric arrangement enables realising such in a relatively small construction volume.

In an embodiment, the circuit board comprises plural conductor layers, the signal conductor comprises a signal trace on a signal layer in the circuit board and the circuit board comprises at least one ground trace, in particular a wide trace such as a plane, e.g. a ground plane, on a conductor layer adjacent the signal layer, the ground trace and/or ground plane overlapping and shielding the signal trace, when viewed along a normal to the layers. Preferably the circuit board comprises at least one such ground trace and/or ground plane on opposite sides of the signal layer. Also, the signal layer may comprise one or more ground traces adjacent the signal trace. Thus, the signal conductor is shielded by ground traces from being affected by noise and/or prevented from itself affecting other signals.

In an embodiment, at least part of the shield extends from a first side of the circuit board in a nonzero angle, in particular a substantially straight angle relative to the board, so that the shield may be at a suitable angle, e.g. perpendicular, to the board. The shield may comprise a further part extending from a second, opposite side of the circuit board in another nonzero angle, which may differ from or be equal to the aforementioned nonzero angle, in particular a substantially straight angle. The shield and the further shield preferably are arranged opposite each other with respect to the circuit board, extending from opposite sides of the board. The shield and the further shield may overlap when viewed along a normal to (one or more layers of) the board.

Thus, the signal conductor may traverse the shield by means of the circuit board and the shield may shield against emissions from and/or immisions into elements mounted on the circuit board. Shields extending in opposite directions from the circuit board may provide shielding on both sides of the board and may facilitate connection with other components in the device.

In an embodiment, the plurality of surface mount capacitors comprises a first plurality of surface mount capacitors and a second plurality of surface mount capacitors arranged on opposite sides of the shield on the circuit board, wherein the first and second pluralities of surface mount capacitors may have equal capacitances. Thus, a signal impedance may be tailored to the traverse. Providing equal capacitances may reduce or prevent impedance variations and/or signal degradation, e.g. reflection and/or absorption loss, in the feedthrough capacitor system.

Accordingly and advantageously, the first and second pluralities of surface mount capacitors may be provided as mirror images of each other with respect to the capacitances and positions of the individual capacitors relative to the shield and/or with respect to a main direction of extension of the signal conductor between the first and second pluralities of surface mount capacitors. Thus, symmetry of the feedthrough capacitor system may be increased, improving predictability and reliability of the system over an increased frequency range.

One or more properties, preferably all properties, of all of the surface mount capacitors may be substantially identical, e.g. the surface mount capacitors having the same capacitance, rated voltage, construction, etc.

The filter may be configured for filtering an AC signal with a frequency in a range of 25 MHz-30 MHz, preferably in a range of 26 MHz-28 MHz, more preferably in a range of 26.96 MHz-27.28 MHz. Such frequencies are of particular interest in physiotherapy for creating electric and magnetic fields in animal tissues, in particular human or other mammalian tissues. By application of such fields to the tissue e.g. due to therewith induced currents in the tissues particular desired physiological effects may be achieved, such as a rise in tissue temperature or nonthermal changes in cellular activity.

The filter may be configured for filtering an AC signal with a power in a range of 2 W-2000 W, preferably in a range of 2 W-750 W, more preferably in a range of 2 W-200 W.

Such powers are of particular interest, considering that a mean power of up to 5 W deposited into the tissue is generally considered to be non-thermal. These lower power levels are applied for acute to subacute conditions including e.g. postoperative pain and postoperative wounds. Research has shown that at mean powers of about 12 Watts or more deposited power, most people can feel some heating effect. These power levels are used for their thermal effects in chronic conditions like e.g. osteoarthritis. Higher powers may cause more significant heating.

In an aspect a high-frequency power generator comprising the electrical device presented herein is provided.

In an aspect a physiotherapy device comprising the electrical device presented herein, e.g. the aforementioned high-frequency power generator, is provided. Through use of inductive electrodes, high-frequency electric currents may be produced within the body of a subject. The energy is absorbed by soft tissues. This results in deep heating of tissue and an increase in cellular metabolism resulting in soft tissue healing.

In a physiotherapy device typical values may be a frequency of about 26-28 MHz, e.g. about 27 MHz, with about 250-350 Volt peak-peak e.g. about 300 Volt peak-peak, and about 150-250 W, e.g. about 200 W, generated power for treatment of a subject with continuous and/or pulsed shortwave electrotherapy.

BRIEF DESCRIPTION OF THE DRAWINGS

The above-described aspects will hereafter be more explained with further details and benefits with reference to the drawings showing a number of embodiments by way of example.

In the drawings.

DETAILED DESCRIPTION OF EMBODIMENTS

It is noted that the drawings are schematic, not necessarily to scale and that details that are not required for understanding the present invention may have been omitted. The terms "upward", "downward", "below", "above", and the like relate to the embodiments as oriented in the drawings, unless otherwise specified. Further, elements that are at least substantially identical or that perform an at least substantially identical function are denoted by the same numeral, where helpful individualised with alphabetic suffixes.

Figures 1A, 1B:
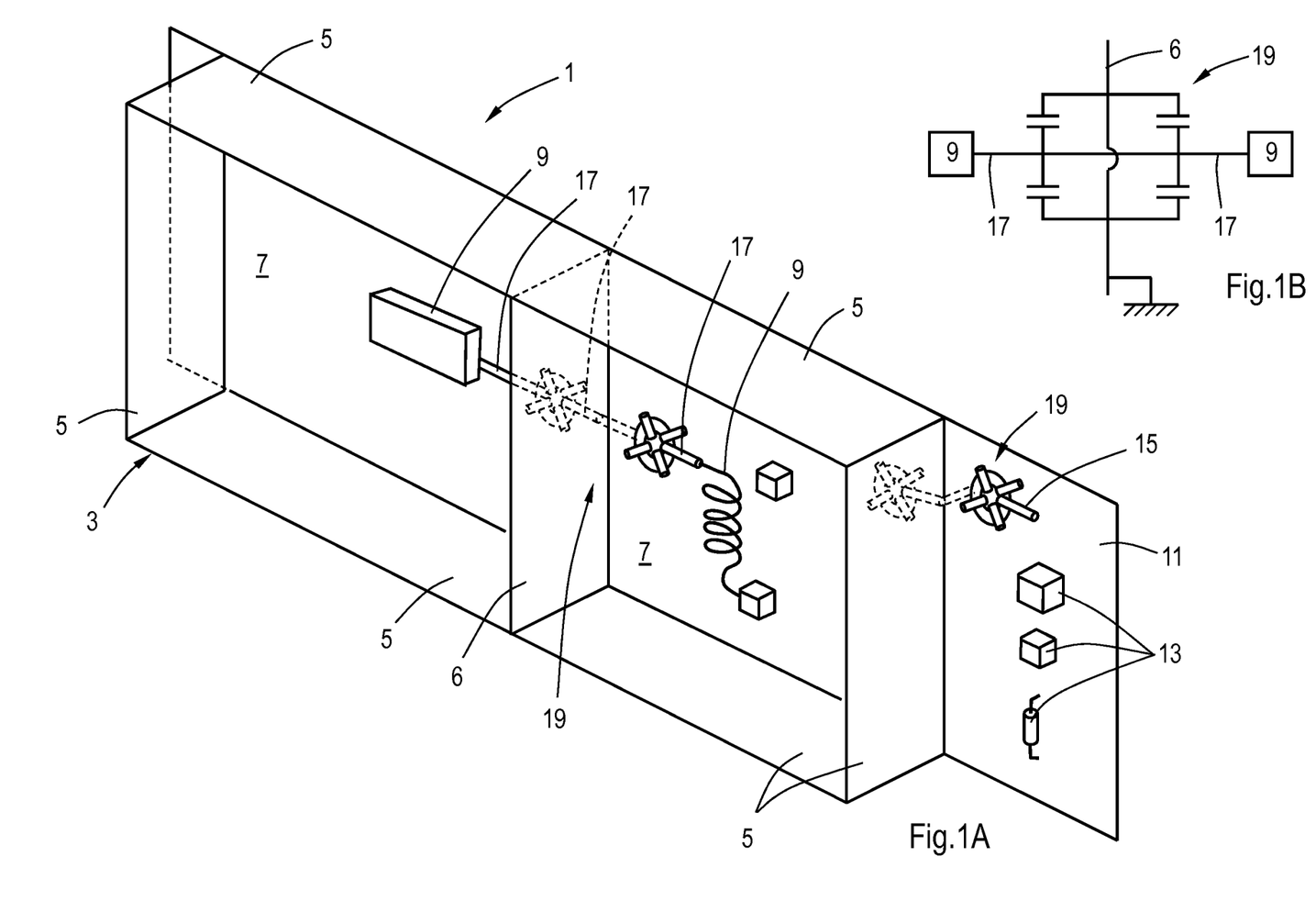
FIG. 1A is a schematic of an embodiment of an electrical device.
FIG. 1B shows an equivalent circuit of a detail of the embodiment of FIG. 1A.

FIG. 1A is a schematic of an electrical device 1 comprising a housing 3 with walls 5, 6, divided in two compartments 7 by dividing wall 6, each compartment 7 surrounding a filter segment 9 of an electrical high frequency filter, e.g. an LC-filter comprising one or more coils and capacitors. The walls 5, 6 of the housing 3 are conductive, e.g. metal or metalized plate material, and form a shield for electromagnetic radiation.

The housing 3 comprises a circuit board 11, here being provided as a printed circuit board (PCB). In this case, the housing 3 is mounted onto a top surface of the circuit board 11, wherein the circuit board 11 extends beyond the walls 5, 6 of the housing 3 and the walls 5, 6 being arranged perpendicular to the circuit board 11. However, in another embodiment, not shown, the circuit board 11 could also be contained fully within the housing and/or one or more of the walls could extend at a non-perpendicular angle to the plane of the circuit board 11. (Electrical) components 13 of the device 1 are mounted onto the circuit board 11 and at least some of them are electrically connected by conductive traces 15 on and/or in the circuit board 11. In the shown embodiment, walls 5, 6 of the housing 3 extend perpendicular to the circuit board 11. One or more compartments 7 may be covered with further wall portions 16, e.g. in the form of a (possibly removable) lid to part of the housing 3 (see FIG. 2A).

Signal conductors 17 traverse the shield walls 5 and operably connect the filter segments 9 to each other and a filter segment 9 to at least one further component 13 for transmitting a signal between the filter segments 9 and to the component 13. Feedthrough capacitor systems 19 are operably arranged between the signal conductors 17 and the shield walls 5, 6.

For optimum filtering results the filter has a plurality of filter segments 9 arranged in series. To prevent unwanted interaction between different filter segments 9, e.g. noise and/or cross talk influences, some of the filter segments 9 are shielded from each other by separation by the dividing shield walls 6 as shown. The signal conductor 17 for carrying the signal that is (to be) filtered by the filter segments 9 electrically connects subsequent filter segments 9 and traverses the shield wall 6 for transmitting the signal from one filter segment 9 to the subsequent filter segment 9. To minimize reflection losses and/or other adverse effects at the traverse, the feedthrough capacitor system 19 is electrically mounted between the signal conductor and the shield wall, as shown in FIG. 1B.

Figure 2A:
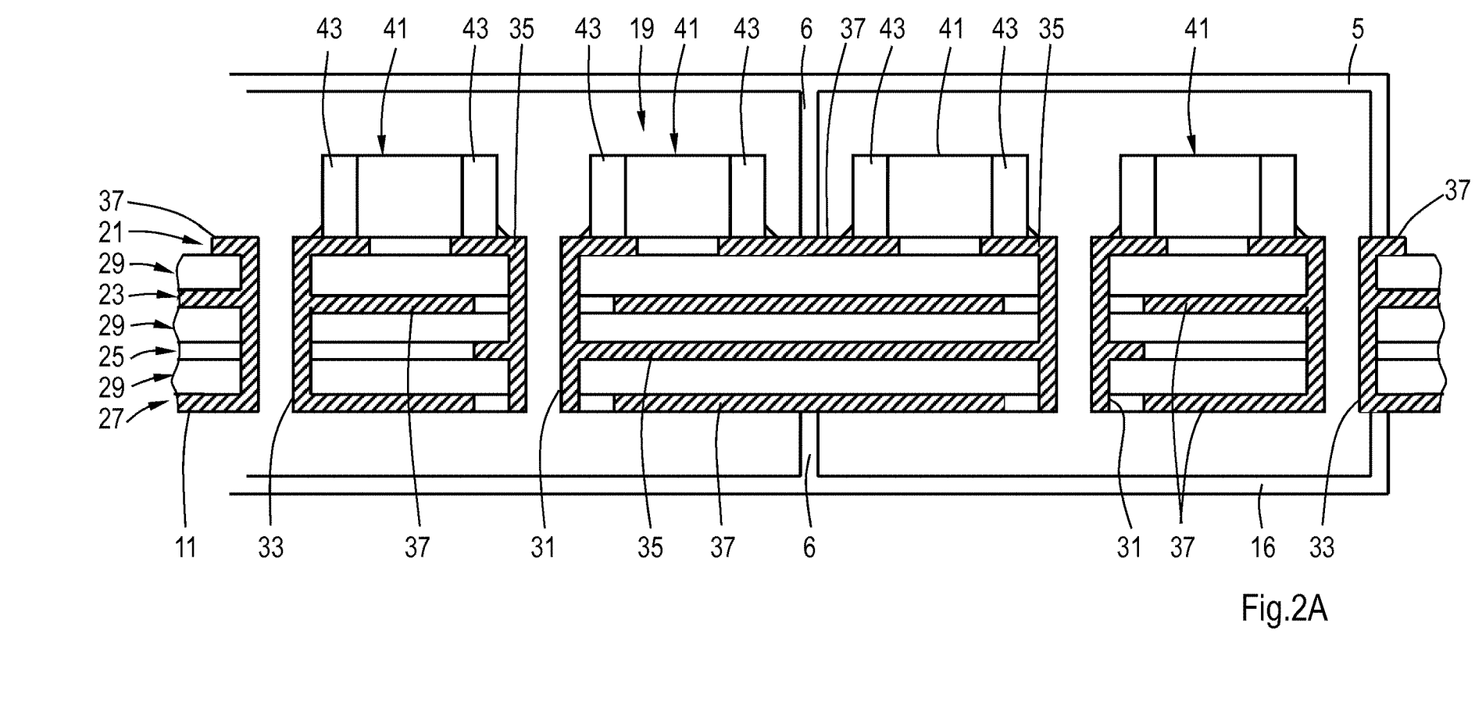
FIG. 2A is a cross section of a detail of an embodiment of an electrical device.
Figure 2B:
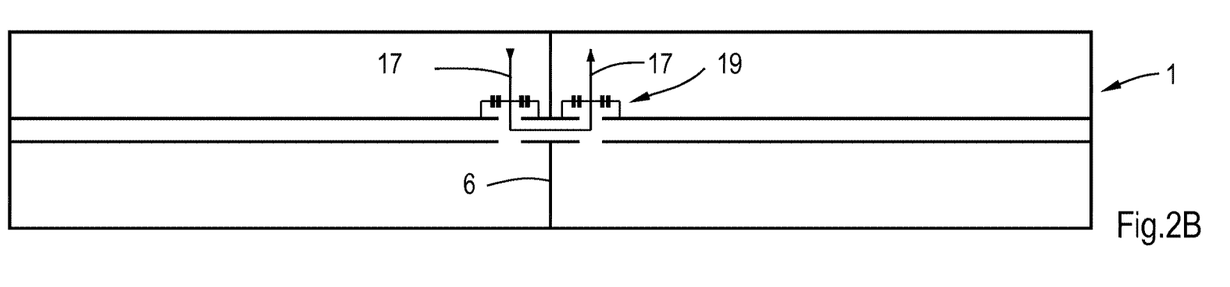
FIG. 2B is a schematic cross section view of another embodiment of an electrical device.
Figure 3A:
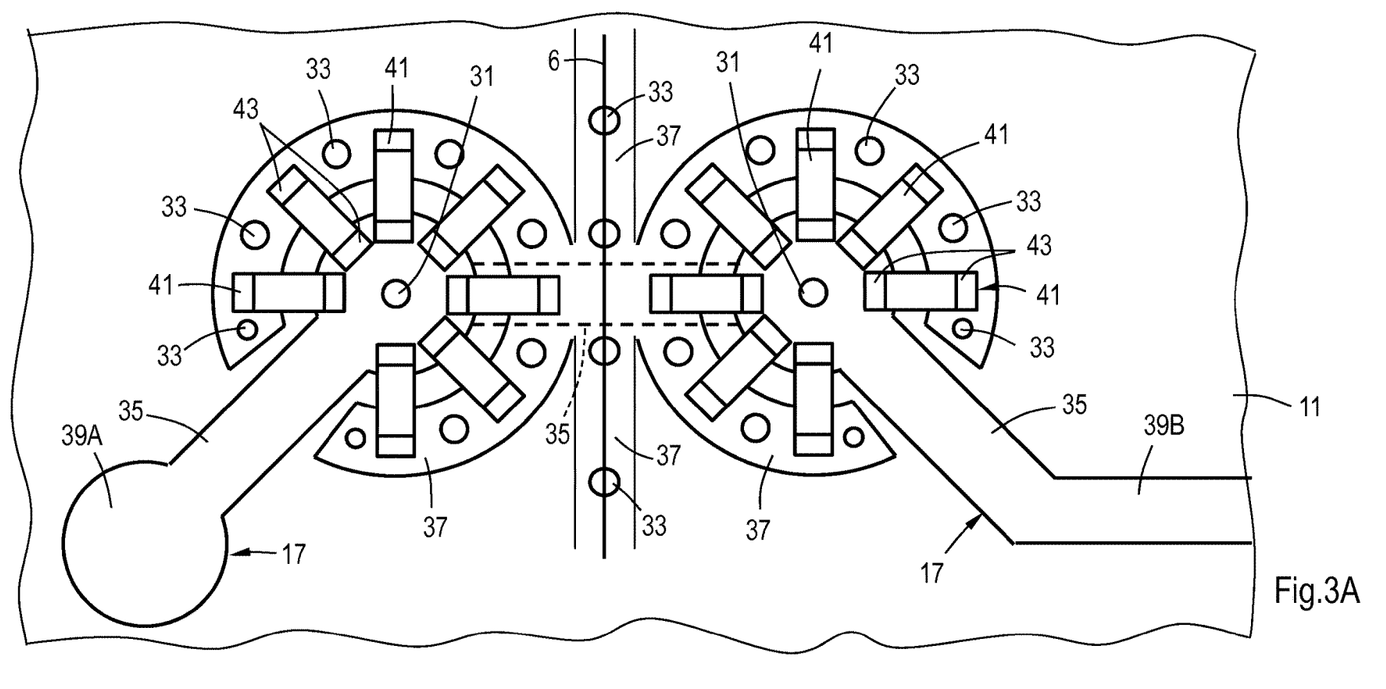
FIG. 3A is a plan view of a detail of an embodiment of an electrical device.
Figure 3B:
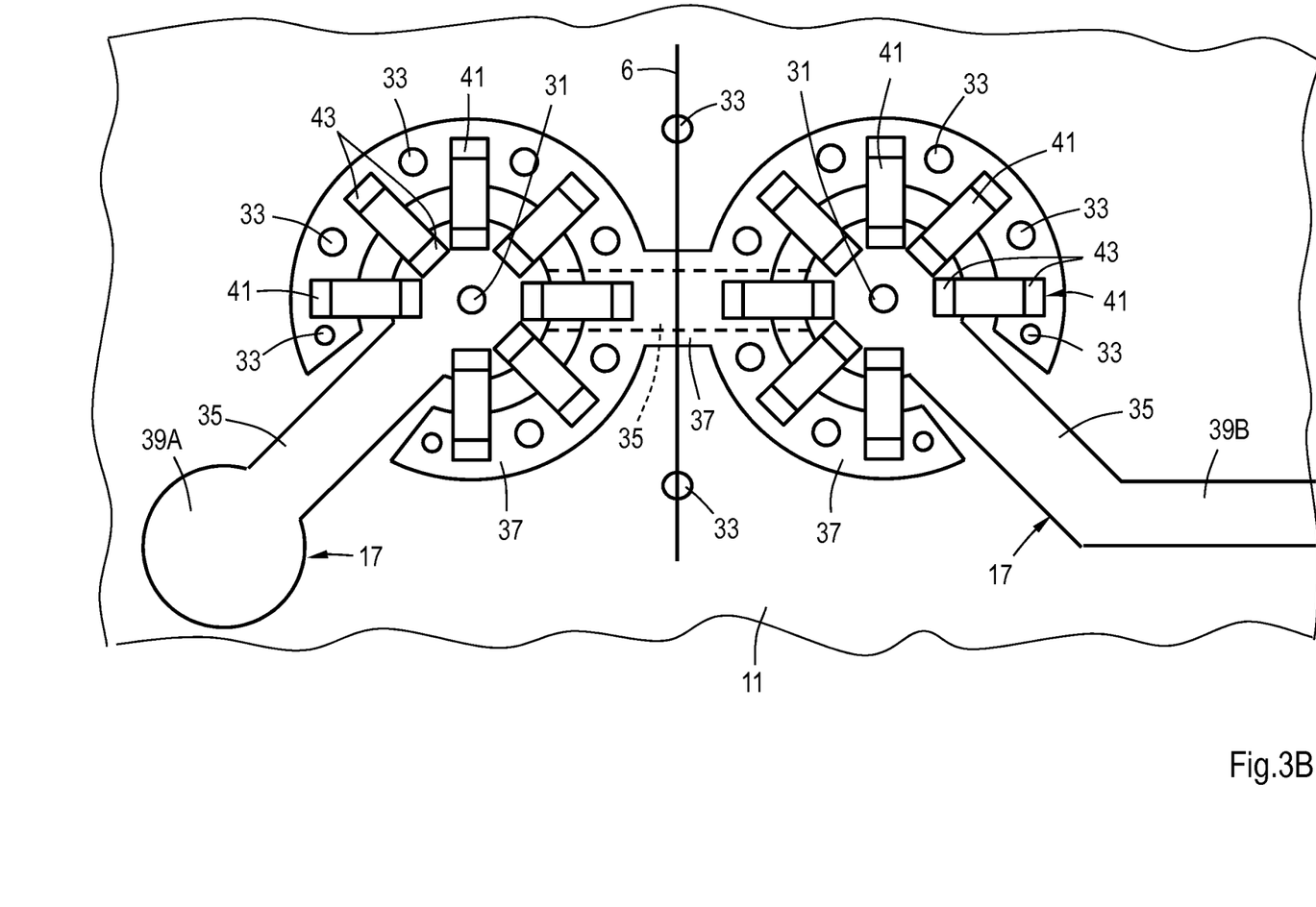
FIG. 3B is a plan view of a detail of another embodiment of an electrical device.

FIGS. 2A and 2B are schematic cross sections of embodiments of a feedthrough capacitor system 19. FIGS. 3A and 3B are schematic top views of embodiments of a feedthrough capacitor system 19. FIGS. 2A, 3A and 3B show the respective feedthrough capacitor system 19 traversing a shield wall 6, the respective feedthrough capacitor systems 19 having the same basic construction.

In FIG. 2A, walls 5, 6, 16 are shown to extend on opposite sides of the PCB 11 so that the feedthrough capacitor system 19 and other electrical components (not shown) are surrounded and shielded on both sides of the circuit board 11. The circuit board 11 comprises conductive layers 21, 23, 25 and 27 that are electrically insulated from each other, in particular a top (signal) layer 21, a ground layer 23, a middle signal layer 25 and a bottom (ground) layer 27 each carrying conductive traces (see below) and neighbouring layers being separated from each other by insulation layers 29. Note that in other embodiments a circuit board may have less or more layers, and any layers may be differently arranged.

A plurality of conductive vias 31, 33, here: plated vias, are provided through at least part of the circuit board 11 and connect traces on particular layers 21, 23, 25, 27, through one or more intervening layers 23, 25, 27, 29, so that vias 31 connect signal traces 35 on the top layer 21 to signal traces 35 on a signal layer 25 forming signal vias 31, and the vias 33 connect ground traces 37 on the top layer 21 to ground traces 37 on a ground layer 23, 27, forming ground vias 33. The shield walls 5, 6 are electrically connected and possibly mechanically connected to ground traces 37, e.g. by soldered connections And/or by conductive elastomers. The shield 6 is optionally electrically connected to ground vias 33 for further assuring a common potential for the ground layers and the shield.

Signal traces 35 and/or ground traces 37 may extend on the respective conductor layers in various shapes and connect various circuit elements, e.g. the shield 6 (FIG. 3A) and/or connecting through contact pads 39A, 39B (FIGS. 3A, 3B).

Surface mount capacitors 41 are surface mounted onto the traces 35, 37 on the top layer 21. The surface mounting comprises electrically and mechanically attaching contacts 43 of the capacitors 41 to the signal and ground traces 35, 37, respectively e.g. by soldering and/or or using a conductive adhesive. Thus, the terminals 43 of the capacitors 41 are electrically connected to the signal conductor 17 on one side and the shield 6 on the other side with the dielectric portion of the capacitors 41 in between. The capacitors 41 on each side of the shield 6 are electrically arranged in parallel to each other, so that their individual capacitances $C_i$ add linearly to a combined equivalent capacitance $C_{eq}$ and their inductances $L_i$ add reciprocally to a combined equivalent inductance $L_{eq}$ per side.

Thus, referring to FIGS. 2 and 3, a continuous signal conductor 17 is formed by a signal trace 35 on the top layer 21, e.g. starting at contact pad 39A, a signal via 31 into the circuit board 11, a signal trace 35 on signal layer 25 within the circuit board 11 (indicated in broken lines in FIG. 3) which traverses the shield 6, another signal via 31 and another signal trace 35 on the top layer 21.

Similarly, continuous ground conductors are provided by the ground traces 37 and ground vias 33, wherein the ground conductors are electrically connected to the shield, and in the shown embodiment also being mechanically connected to the latter. Best seen in FIG. 3 is that in plan view of the circuit board 11 a ground trace 37 on the top layer 21 of the circuit board 11 overlaps the signal trace 35 within the circuit board 11 and here also is chosen to be wider than that signal trace 35 and in the embodiment of FIG. 3A the ground trace 37 is extended along the shield 6 to serve as a ground connection for the shield 6. A similar and possibly substantially identical ground trace may be arranged on a ground layer 27, which layer may also be substantially entirely conductive across a surface occupied by a filter segment 9, a compartment 7, or the entire circuit board 11. Additional ground traces may extend adjacent, and possibly parallel to, the signal trace 35 on a signal layer 25 within the circuit board 11.

The embodiment of FIG. 2B, as schematically shown, differs in that the signal conductor 17 extends as wire conductors 45 on opposite sides of the feedthrough capacitor system 19, and not as circuit board traces 35.

Thus a signal conductor is provided traversing the shield 6 for transmitting a signal from one side of the shield to the opposite side of the shield and being provided with a feedthrough capacitor system 19. Best seen in FIG. 3 is that in this embodiment the arrangement of the feedthrough capacitors on each side is chosen to be symmetric about the respective signal trace and here also about the respective signal via 31. Further, the arrangements of the capacitors 41 on opposite sides of the shield wall 6 are chosen to be substantially mirror images from each other.

Due to the close shielding provided by the ground traces on ground layers close to the signal traces a compact device is provided and (escape of) noise frequencies may be kept to a minimum also in case of high frequencies and high powers. Predictability, reliability and robustness in mechanical and electrical sense are increased relative to free-standing conductors (i.e. not mounted onto or integrated in a circuit board)

The disclosure is not restricted to the above described embodiments which can be varied in a number of ways within the scope of the claims. For instance capacitors need not be positioned as drawn but can be grouped otherwise, also the number of capacitors on both sides of the shield need not be equal in number or size.

Elements and aspects discussed for or in relation with a particular embodiment may be suitably combined with elements and aspects of other embodiments, unless explicitly stated otherwise.

The invention claimed is:

1. An electrical device comprising an electrical high-frequency filter and a shield separating the filter from at least one further electrical component of the device,
   wherein the filter is configured for filtering an AC signal with a frequency in a range of 25 MHz-30 MHz,
   the device further comprising a signal conductor which operably connects the filter to the further component and traverses the shield for transmitting the AC signal from the filter to the component,
   a feedthrough capacitor system of the filter being electrically arranged between the signal conductor and the shield,
   wherein the feedthrough capacitor system comprises a plurality of surface mount capacitors electrically arranged between the signal conductor and the shield, the surface mount capacitors being surface mounted on a circuit board.

2. The electrical device according to claim 1, wherein the filter is a filter segment and the further electrical component is a further filter segment, these filter segments together forming at least part of a sequential filtering device.

3. The electrical device according to claim 1, wherein the shield is part of a housing at least partly surrounding and shielding the filter.

4. The electrical device according to claim 3, comprising plural said housings each at least partly surrounding and shielding at least one said filter.

5. The electrical device according to claim 1, wherein in the feedthrough capacitor system the signal conductor extends at least partly on and/or in the circuit board as a signal trace on and/or in the circuit board and/or as a signal via through at least part of the circuit board.

6. The electrical device according to claim 1, wherein the circuit board comprises a ground trace and/or a conductive ground via which is electrically connected to the shield.

7. The electrical device according to claim 3, wherein the surface mount capacitors are surface mounted to the signal conductor and to a ground trace of the circuit board.

8. The electrical device according to claim 1, wherein a plurality of the one or more surface mount capacitors is mounted symmetrically around at least part of a signal portion on the circuit board.

9. The electrical device according to claim 1, wherein the circuit board comprises plural conductor layers, the signal conductor comprises a signal trace on a signal layer in the circuit board, the circuit board comprises at least one ground trace and/or a ground plane-on a conductor layer adjacent the signal layer, the ground trace and/or ground plane overlapping and shielding the signal trace.

10. The electrical device according to claim 1, wherein at least part of the shield extends from a first side of the circuit board at a nonzero angle.

11. The electrical device according to claim 1, wherein the plurality of surface mount capacitors comprises a first plurality of surface mount capacitors and a second plurality of surface mount capacitors arranged on opposite sides of the shield on the circuit board.

12. The electrical device according to claim 11, wherein the first and second pluralities of surface mount capacitors are provided as mirror images of each other with respect to the capacitances and positions of the individual capacitors relative to the shield and/or with respect to a main direction of extension of the signal conductor between the first and second pluralities of surface mount capacitors.

13. The electrical device according to claim 1, wherein the filter is configured for filtering the AC signal with a power in a range of 2 W-2000 W.

14. A physiotherapy device comprising the electrical device according to claim 1.

15. The physiotherapy device according to claim 14, configured for treatment of a subject with continuous and/or pulsed shortwave electrotherapy, wherein the filter is configured for filtering a frequency of about 26-28 MHz, with about 250-350 Volt peak-peak and about 150-250 W, generated power.

16. The electrical device according to claim 1, wherein the filter is configured for filtering an AC signal with a frequency in a range of 26.96 MHz 27.28 MHz.

17. The electrical device according to claim 6, wherein the ground trace and/or the conductive ground via is also mechanically attached to the shield.

18. The electrical device according to claim 8, wherein a plurality of the one or more surface mount capacitors is mounted substantially radially symmetrically around a via.

19. The electrical device according to claim 9, wherein the circuit board comprises at least one said ground trace and/or ground plane on opposite sides of the signal layer and wherein the signal layer comprises ground traces adjacent the signal trace.

20. The electrical device according to claim 10, wherein the shield comprises a further part extending from a second, opposite side of the circuit board at a nonzero angle and the shield and the further shield are arranged opposite each other with respect to the circuit board.

21. The electrical device according to claim 1, wherein:
   the filter is a first filter and the at least one further electrical component is a second filter such that the shield separates the first filter from the second filter;
   the plurality of surface mount capacitors of the feedthrough capacitor system comprises (i) a first subset of surface mount capacitors and (ii) a second subset of surface mount capacitors; and
   the shield is conductive and is electrically connected to a ground for the plurality of surface mount capacitors of the feedthrough capacitor system.

22. The electrical device according to claim 21, wherein the first and second filters are configured for filtering the AC signal having a power in a range of 2 W-2000 W.

* * * * *